United States Patent [19]

Heath et al.

[11] Patent Number: 5,356,622

[45] Date of Patent: Oct. 18, 1994

[54] FLEA MIDGUT-SUPERNATANT VACCINES

[75] Inventors: Andrew W. Heath, Menlo Park; Miles Yamanaka, Redwood City; Ann Arfsten, Fremont; Beverly Dale, Los Altos, all of Calif.

[73] Assignee: Paravax, Inc., Fort Collins, Colo.

[21] Appl. No.: 806,482

[22] Filed: Dec. 13, 1991

[51] Int. Cl.$^5$ .............................................. A61K 39/35
[52] U.S. Cl. .................... 424/265.1; 530/427; 530/858; 514/830
[58] Field of Search ................ 424/88; 530/389.1, 413

[56] References Cited

PUBLICATIONS

Johnston, L. A. Y. et al. (1986) Int. J. Parasitol. 16:27–34.
Azad, A. F., et al., Am. J. Trop. Med. Hyg. (1987) 37:629–635.
Cherney, L. S., et al., Am. J. Trop. Med. (1939) 19:327–332.
Chinzei, Y., et al., Med. Vet. Entomol. (1987) 1:409–416.
Halliwell, R. E. W., J. Immunol. (1973) 110:442–430.
Halliwell, R. E. W., et al., J. Allerg. Clin. Immunol. (1978) 62:236–242.
Halliwell, R. E. W., et al., Vet. Immunol. Immunopathol. (1985) 8:215–223.
Kemp, D. H., et al., Internat. J. Parasitol. (1986) 16:115–120.
Kwochka, K. W., Vet. Clin. North Am. (1987) 17:1235–1262.
Nesbitt, G. H., et al., J. Am. Vet. Med. Assoc. (1978) 173:282–288.
Opdebeeck, J. P., et al., Immunol. (1988) 63:363–367.
Opdebeeck, J. P., et al., Parasite Immunol. (1988) 10:405–410.
Opdebeeck, J. P., et al., Immunol. (1989) 67:388 a Pre--Publication copy is submitted herewith.
Rand, K. H., et al., Proc. Natl. Acad. Sci. (USA)(1989) 86:9657–9661.
Ribiero, J. M. C., Ann. Rev. Entomol. (1987) 32:463–478.
Schlein, Y., et al., Physiolog. Entomol. (1976) 1:55–59.
Soulsby, E. J. L., in Helminths, Arthropods, and Protozoa of Domesticated Animals, 7th ed., (1982), Lea and Febiger, eds., Philadelphia, Penna. pp. 378–384.
Vaughn, J. A., et al., J. Med. Entomol. (1988) 25:472–474.
Wikel, S. K., Vet. Parasitol. (1984) 14:321–329.
Wikel, S. K., Vet. Parasitol. (1988) 29:235–264.
Willadsen, P., et al., J. Immunol. (1989) 143:1346–1351.
Wong, J. Y. M. & J. P. Opdebeeck, Immunol. (1989) 66:149.

Primary Examiner—Christine M. Nucker
Assistant Examiner—Julie Krsek-Staples
Attorney, Agent, or Firm—Morrison & Foerster

[57] ABSTRACT

A vaccine for protecting avian and mammalian subjects against flea infestation comprises the supernatant fraction of flea midgut, or the antigenic components thereof. This also has the effect of reducing flea populations in the environment of the subject. Antibodies raised by these vaccines are also useful in purification and diagnosis.

4 Claims, 6 Drawing Sheets

FLEA MIDGUT-SUPERNATANT VACCINES

TECHNICAL FIELD

The invention relates to prevention of flea infestation in mammals and birds. More particularly, the invention concerns vaccines derived from soluble extracts of midguts derived from blood-fed fleas. These vaccines are used to immunize mammalian and avian subjects against flea infestation, and to generate antibodies for passive therapy.

BACKGROUND ART

Fleas are insects which behave as ectoparasites for birds and mammals. They are a serious nuisance both in the raising of animals which are sources of food and fiber and in the nurture of pet cats and dogs. The problem in the latter situation is particularly serious because the infestation also becomes a source of annoyance for the pet owner who may find his or her home generally contaminated with fleas which feed on the pets, and these parasites can induce an allergic reaction in both the pets and humans. The prevalence of flea allergic dermatitis (FAD) constitutes the foremost veterinary dermatological problem in the U.S. (Kwochka, K. W., *Vet Clin. North Am* (1987) 7:1235-1262). Furthermore, the life cycle of the flea favors a survival of intermediate stages since the adult flea feeds and copulates frequently and contaminates the entire environment with eggs (Nesbitt, G. H., et al., *J Am Vet Med Assoc* (1978) 173:282-288; Soulsby, E. J. L., in *Helminths, Arthropods and Protozoa of Domesticated Animals,* 7th ed. (1982), Lea and Febiger, eds., Philadelphia, Pa., pages 378-384).

Although flea (i.e., insect) parasitism can be distinguished from that associated with other parasites, such as helminths, which are worms, and ticks, which are arachnids, control of all forms of parasitism has generally involved internal or external applications of chemicals. Commonly encountered approaches to control of the flea problem are generally focused on use of insecticides in formulations such as sprays, shampoos, dusts, dips, or foes, or in pet collars. None are notably successful. While some of these products are efficacious, they are often not successful in reducing flea populations on the pet or in the home for one or more of the following reasons: (1) failure of owner compliance (frequent administration is required), (2) behavioral or physiological intolerance of the pet to the pesticide product or means of administration, and (3) the emergence of flea populations resistant to the prescribed dose of pesticide. In addition, some flea-control clients are adverse to the use of certain chemicals in their home or on their pet that will remain as residual contaminants in the environment.

Efforts to find nontoxic approaches to flea control have resulted in the recent introduction of insect growth regulators (IGRs) such as methoprene which mimic flea hormones and affect flea larval development. A vaccine to reduce flea infestation on the pet and in the home would constitute another nonchemical approach to flea control and would avoid many of the compliance issues necessary for correct pesticide or IGR administration.

A number of attempts have been made to provide a vaccination approach to endoparasites, to other ectoparasites, or to ectoparasites in general. Danish patent 2644149 (1978) suggests the use of antigenic extracts from intermediate hosts in order to prepare antiparasitic vaccines. The focus of this work is with respect to Schistosomes. PCT application WO88/01277 to Australian National University discloses recombinant DNA encoding a helminth parasite antigen and suggests its use in constructing vaccines. PCT application WO 87/05513 (U.S. Pat. No. 4,814,170) assigned to Aphton Corporation describes antiendo- or antiectoparasite vaccines in general, which are derived from endocrine products, such as juvenile hormones.

PCT application WO 86/02839 suggests vaccines against helminths which contain suspensions, homogenates or extracts of nonparasitic nematode species. Presumably, these nonparasitic species are closely enough related to the parasitic forms to engender appropriate antibodies. A similar approach with respect to protozoa is disclosed in PCT application WO 83/03199. British application 1580539A published in 1980 suggests an antiparasitic vaccine derived from secretions of the parasite. None of these approaches are specifically directed to protection against flea infestation.

The problem of flea allergic dermatitis (FAD) has, however, inspired considerable study of the immunological response of hosts to flea antigens which are, presumably, made available for host exposure through the saliva. These studies focus on the nature of the immune response in the host to these antigens, which do not necessarily result in protection of the host against infestation (Halliwell, R. E. W., *J Immunol* (1973) 110:442-430; Halliwell, R. E. W., et al., *J Allerg Clin Immunol* (1978) 62:236-242; Halliwell, R. E. W., et al., *Vet Immunol Immunopathol* (1985) 8:215-223; Wikel, S. K., *Vet Parasitol* (1984) 14:321-329). An early study which used FAD as a criterion for response to flea antigens, conducted in 1939, suggested that the FAD response, however, might somehow protect the host in such a way so as to prevent flea bites (Cherney, L. S., et al., *Am J Trop Med* (1939) 19:327-332).

Others have suggested this general concept with regard to other parasites such as ticks and mosquitoes where it is considered that the hypersensitivity generated by salivary antigens may provide some protection against feeding of the parasite (Ribelto, J. M. C., *Ann Rev Entomol* (1987) 32:463-478; Brown, S. J., *Vet Parasitol* (1988) 29:235-264; Wikel, S. K., *Vet Parasitol* (1988): 29:235-264). Since one of the features needed in an effective antiflea vaccine, especially in the context of protecting pets against flea infestation, is the incentive for owner compliance, it is clearly undesirable for any vaccine to behave in such a way as to correlate efficacy with hypersensitivity and dermatitis.

An alternate concept, that of using "hidden" antigens, has been extensively studied for defense against ticks, e.g., *Boophilus microplus* (Opdebeeck, J. P., et al., *Immunol* (1988) 63:363-367; Opdebeeck, J. P., et al., *Parasite Immunol* (1988) 10:405-410; Wong, J. Y. M., and Opdebeeck, J. P., *Immunol* (1989) 66:149; Opdebeeck, J. P., et al., *Immunol* (1989) 67.:388; European patent application 208,507, published Jan. 14, 1987. See also Willadsen, P., et al., *J Immunol* (1989) 143:1346-1351; Rand, K. N., et al., *Proc Natl Acad Sci* (U.S.A.) (1989) 86:9657-9661; PCT application WO 88/3929, published Jun. 2, 1988; Kemp, D. H., et al., *Int J Parasitol* (1986) 16:115-120). This approach is also reviewed by Wikel, S. K., (*Vet Parasitol* (1988) (supra)). This approach has also been attempted using the thoracic muscles of the stable fly (Schlein, Y., et al., *Physi-*

*olog Entomol* (1976) 1:55-59). Furthermore, it has been shown that IgG components from the host can be found intact in the body cavity of the parasitic insect which indicates the passage of immunogobulin through the midgut wall (Chinzei, Y., et al., *Med Vet Entomol* (1987) :409-416; Hatfield, P. R., *Med Vet Entomol* (1988) 2:339-345; Vaughan, J. A., et al., *J Med Entomol* (1988) 25:472-474). While this phenomenon of immunogobulin passage through the gut wall has also been shown in fleas, the work related not to antibodies to flea antigens, but rather to antibodies formed to rickettsia organisms carried in the flea (Azad, A. F., et al., *Am J Trop Med Hyg* (1987) 37:629-635).

More recently, a thesis prepared in support of the award of a Ph.D. degree at the University of London by Hatfield, P. R. (1986), investigated the immunization of hosts with homogenates or crude extracts of mosquitoes and fleas. The study showed that fleas that fed on mice immunized with flea homogenates and that ingested flea-specific antibodies showed a significant increase in mortality. Similar results were obtained for mosquitoes. The flea aspect of the study used *X. cheopis* and utilized a solubilized extract of whole body homogenates prepared from newly hatched, unfed fleas.

Copending application U.S. Ser. No. 07/571,257, filed Aug. 22, 1990, now abandoned, describes the preparation of antiflea vaccines from the membranous elements of fed and unfed flea populations. Both full body membrane fractions and midgut membrane fractions were employed.

The present invention, in contrast, utilizes supernatant flea antigens, preferably from the fed midgut. The antigens in the supernatant provide nonallergic vaccines that are capable of immunizing conventional hosts against flea infestation, and furthermore raise antibodies which can be used for passive immunization.

DISCLOSURE OF THE INVENTION

The invention provides a vaccine useful to immunize mammalian and avian subjects in such a manner as to lower infestation by the insect ectoparasites which are responsible for the problems associated with extensive flea infestation, and to lower the population of fleas in the surrounding environment. The vaccine employs antigens which are derived from the supernatant fraction of extracts from midgut, preferably fed midgut, of the major parasitic fleas of dogs and cats, e.g., *Ctenocephalides felis*, and provides nonallergic protection against this nuisance.

Therefore, in one aspect, the invention is directed to a vaccine for protection of a subject against infestation by fleas, which vaccine comprises an amount of the supernatant fraction of a flea midgut, or an effective antigenic component of said supernatant, which is effective to confer resistance to the infestation, either by killing the insects or by incapacitating them in some way, or both. The successful application of the vaccine also lowers the flea population in the animal's surroundings. The invention is also directed to antibodies specifically immunoreactive with these antigens. In an additional aspect, the invention is directed to a method to protect a subject against infestation by fleas and to reduce the flea population in its environment which comprises administering the antigen-containing vaccine of the invention. In another aspect, the invention relates to passive immunotherapy using the invention antibodies. In still another aspect, the invention is directed to methods to prepare the effective vaccines.

MODES OF CARRYING OUT THE INVENTION

The invention vaccines are supernatant fractions derived from the midgut sections of fleas, preferably fed flea midguts. By "supernatant" is meant the soluble components associated with the midgut tissue which are leached from the tissue when suspended in buffer and/or which are soluble in the lysate obtained when the cells are sonicated. The "supernatant" thus contains at least one soluble antigen, putatively a protein antigen. The antigenmay be used directly as a vaccine or may be used to raise antibodies which are then used in passive immunotherapy or in diagnosis. The vaccines are formulated in conventional ways, optionally using adjuvants either in or along with the formulation. Low molecular weight antigens are also conjugated to carriers or to themselves if necessary to enhance immunogenicity.

PREPARATION OF SOLUBLE MIDGUT COMPONENTS

Large numbers of fleas are readily obtained using growth on whole animal hosts, such as cats. Alternatively, fleas can be grown using artificial feeding systems such as those described by Wade, S. E., et al., *J Med Entomol* (1988) 25:186-190. Preferred flea sources are those of the species *Ctenocephalides felis*, which is the most common species found infesting domestic animals. However, it is expected that cross-reactivity of antibodies prepared with respect to *C. felis* will be found in other species. The supernatants derived from the midguts of either fed or unfed fleas may be used; however, fed midguts are preferred. It is known that feeding effects differentiation in the midgut of fleas, as is described by Billingsley, P. F., *Ann Rev Entomol* (1990) 35:219-248. As described in this article, feeding results in a deformation of the cells, the release of electron-luscent vesicles into the lumen, and increases in the RER, Golgi, microbodies, lipid vesicles and lyzosomes, as well as elongation of the midgut.

By "fed" fleas is meant that the fleas from which the preparations are derived have been allowed to consume a blood meal for a 24-48 hour period either on animals or by artificial feeding prior to preparation of the supernatant. In the case of "unfed" fleas, newly emerged fleas that have never taken a blood meal are used to prepare the supernatants.

The midguts are dissected from either fed or unfed fleas in the same manner. Live fleas are chilled on ice and placed on a glass slide in a drop of buffer containing physiological saline and EDTA (0.15 M PBS/1 mM EDTA). The head is removed with a scalpel, and the gut is removed through the incision by pushing with dissection needles or scalpel blade. The Malpighian tubules are trimmed away from the gut with needles, and the intact midgut, with proventriculus and hindgut attached, is removed to an aliquot of fresh buffer and stored at $-70°$ C.

To obtain the supernatant fraction containing soluble antigens, the dissected midgut fractions are used in aliquots of about 1000 midguts. The frozen midguts are thawed on ice in 1.5 ml microfuge tubes and then spun at a low speed to pellet the cellular matter. The supernatants are removed and pooled.

The pelleted midguts are then resuspended in the same buffer. Maintaining the aliquots at 1000, these suspensions are then homogenized in a glass/glass tissue homogenizer on ice to a smooth suspension, and then sonicated for two minutes. The sonicated material is then again maintained in a 1000-midgut aliquot pool and spun at about 100,000$\times$g. The supernatant is removed and combined with the original low-speed supernatant to obtain the soluble fraction containing the antigens of the invention.

As a control, the pellet was also resuspended in the same buffer and again homogenized and sonicated. This constitutes the membrane fraction.

Samples may be removed for protein determinations and protease assays (aprotinin is added to the samples at a concentration of 20 $\mu$g/ml) and the remaining materials are stored at $-70°$ C. until used. Typical protein yields from a 1000-midgut aliquot are $\sim$333 $\mu$g from unfed membrane; $\sim$2 mg from fed membrane; and 900 $\mu$g from fed supernatant.

In general, the preparation of the supernatant derived from the flea midguts involves soluble components leached from the midgut cells combined with those soluble proteins which form a portion of the lysate of these cells.

Once obtained, the supernatant fraction is useful as a source of purified antigen components which can be isolated using immunoaffinity columns wherein the affinity ligand comprises monoclonal or polyclonal antibodies raised by administration of the supernatant, or a fraction of the serum, or other conventional separation techniques. It will be understood that when an antibody preparation is in fact recovered, the entire antibody need not be used in all applications, but only the immunologically reactive portions thereof, such as the FAB, FAB' and FAB'$_{(2)}$ fragments. Thus, as used herein, "antibodies" includes the complete antibody molecule as well as the immunologically reactive fragments thereof. Antigen-antibody complexes formed during such affinity-based purifications can also be used for immunization and protection.

For the antigenic components of the soluble supernatant fraction which are of low molecular weight, conjugation to carrier to enhance immunogenicitymay be desirable. Suitable carriers include, for example, keyhole limpet hemocyanin (KLH), animal or human serum albumin, and diphtheria or tetanus toxoid. Conjugation is by conventional means, depending on the nature of the antigen. The antigen can often be coupled directly to carrier, but more frequently a linker, such as those commercially available from Pierce Chemical Company, Rockford, Ill., is used. The linkages employed are those conventionally used, such as amide bonds, thioesters, and disulfides. Alternatively, antigens may be polymerized or crosslinked, for example, with glutaraldehyde, enhancing immunogenicity by increasing perceived molecular weight or presenting novel immunogenic epitopes.

The availability of the supernatants from flea midguts and the ability of the antigens therein to raise antibodies facilitates the preparation of recombinant materials encoding the antigens. mRNA prepared from the whole organism, or preferably the midgut per se, is used as a substrate for reverse transcription into a cDNA library containing fragments encoding the relevant supernatant antigens. This cDNA is cloned into an expression library, such as the $\lambda$-gt system, and the antibodies raised against the supernatant are used to detect the production of antigen from these vectors. Expression clones which produce protein recognized exclusively by the soluble supernatant obtained from flea midguts, as opposed to membrane extracts, are recovered, amplified, and sequenced. Once obtained, the cDNA encoding the appropriate antigens may be ligated into expression systems, as is generally understood in the art and used as a source of production for the antigen.

Further refinement of the cDNA library screening technique results from the use of monoclonal antibodies, obtained as a result of immunization with the supernatant fraction, which are prescreened for their ability to kill or debilitate the parasites as assessed by an artificial feeding assay.

Recombinant production of the desired antigen can be effected in a variety of hosts, including procaryotic and eucaryotic hosts. Especially preferred is the use of the baculovirus/insect cell system. The proteins may be produced either in secreted form or contained intracellularly and recovered by lysis of the cells. The antigens are then purified to the extent necessary to permit their use in vaccines or in assays.

PREPARATION OF ANTIBODIES AND VACCINE COMPOSITIONS

The antigenic composition derived from the midgut supernatant is administered in an immune protocol of multiple dosages at appropriate protein concentrations. Approximately 10–1000 $\mu$g per dose is a preferred range. It is advantageous to use adjuvants, such as Quil A (saponin), RIBI adjuvant, complete or incomplete Freund's adjuvant (CFA or IFA), aluminumphosphate/alum, or one or more of the ISCOMs, or muramyl dipeptide (MDP), depending on the subject. For administration of the vaccine to dogs, RIBI adjuvant or alum is preferred. For use as a vaccine for cats, saponin at concentrations to 400 $\mu$g/ml or RIBI at suitable concentrations are used in a total volume of 0.5–1 ml per injection. Standard formulations for vaccines in general are usable and such formulations can be found in *Remington's Pharmaceutical Sciences,* Mack Publishing Company, Easton Pa., latest edition. Administration is generally systemic by injection, usually intramuscular or subcutaneous injection. Intravenous injection is, for the most part, impractical for veterinary use.

Suitable subjects are those animals who are targets of flea parasitism. These are notably domestic animals such as cats and dogs, farm animals, such as cows, pigs, sheep and horses, and various domesticated birds, such as chickens. Experimental animals such as rabbits, rats and mice may also be immunized specifically for antibody production. The precise nature of the immunization regimen is readily determined using routine optimization procedures, and the general parameters for administration to a specific subject are well known to those of ordinary skill in the art. The dosage levels and the nature of the formulation, of course, varies with the nature of the subject and the severity of the infestation, as well as the precise vaccine active ingredient employed.

The results of vaccination as described above are severalfold. First, the vaccinated animals are protected against flea infestation in that the number of fleas found feeding on the animals directly subsequent to vaccination, even after challenge by artificially introducing a flea population, is greatly reduced. Also, feeding fleas that survive may have markedly reduced fecundity. Thus, the animals per se are protected from the parasitism of the insects.

Second, the immunized animals are useful as sources of antibodies immunoreactive with the specific antigens in the supernatants in diagnostic assays and in passive therapy. Antisera are recovered from these animals and used directly, for example, as affinity purification ligands or as detection reagents to analyze for the presence or absence of antigen, or the antibody-secreting cells such as spleen or peripheral blood lymphocytes are recovered, immortalized, and screened for their ability to secrete antibodies specific for the supernatant antigens. Conventional methods to obtain monoclonal antibody-secreting cells using immunized animals are well known in the art. The immortalized cell lines can be screened using conventional immunoassays employing, as test antigen, the appropriate midgut supernatant or fraction or purified component thereof.

The polyclonal or monoclonal antibodies are, thus, also useful for immunodiagnostic assays for the corresponding antigen or as competitive reagents to assess the levels of antibodies, and are also formulated into passive vaccines to establish immediate resistance to infestation. The antibodies are also useful as affinity reagents for the purification of the antigenic components of the midgut supernatants.

Third, by reducing the susceptibility of the vaccinated animal to feeding by the parasite, the viability of the flea population in the environment of the vaccinated animal is also reduced. Thus, not only is protection conferred on the animal per se, but the environment is de-infested by effective flea population control.

Antibodies prepared with respect to the fed or unfed midgut supernatant preparations are especially useful as affinity reagents to purify the particular individual effective antigens contained in the supernatants. Thus, for example, in one suitable protocol, a supernatant is prepared from the midguts of fed or unfed fleas according to the protocol described hereinabove and outlined in FIG. 6. The resulting supernatant is then applied to an affinity column containing a solid support to which has been coupled the antibody preparation as set forth above under conditions wherein the effective antigenic component is adsorbed to the column. The column is then eluted using suitable protocols such as variation of pH and salt content of the eluting solution and the fractions assayed for protein content and/or immunoreactivity with the antibody preparation. The method of assay may depend on the nature of the eluting buffer; the adsorbed antigen may be eluted from the affinity support per se, and thus assayed by immunoassay or may be eluted in the form of the complex from which the antigen is then recovered. Elution of such complexes may be detected by suitable immunoassay with, for example, a secondary antibody or antibody fragment. The recovered antigen may then be further purified if necessary and formulated individually into vaccines.

The following examples are intended to illustrate but not to limit the invention.

EXAMPLE 1

Production of Supernatant Antigens

In addition to the supernatant antigens of the invention, control antigens were prepared from fed and unfed flea midgut membranes. Unfed *C. felis felis* were from colonies maintained at Louisiana State University (75%), EL-Labs, Soquel, Calif. (20%), and Kansas State University (5%). Fed *C. felis felis* fleas for midgut dissections were placed on cats after emergence and allowed to feed for 36–48 hours prior to collection by manual combing. These fleas were obtained from EL-Labs (60%) and Kansas State University (40%).

In all cases, live fleas were chilled on ice and placed on a glass slide on a drop of buffer containing physiological saline and EDTA. The head of each flea was removed with a scalpel, and the gut was removed through the incision by pushing with dissection needles or scalpel blades. The Malpighian tubules were trimmed away from the gut with needles, and the intact midgut with, the proventriculus and hindgut attached was removed to an aliquot of fresh buffer and stored at $-70°$ C.

Figure 6:
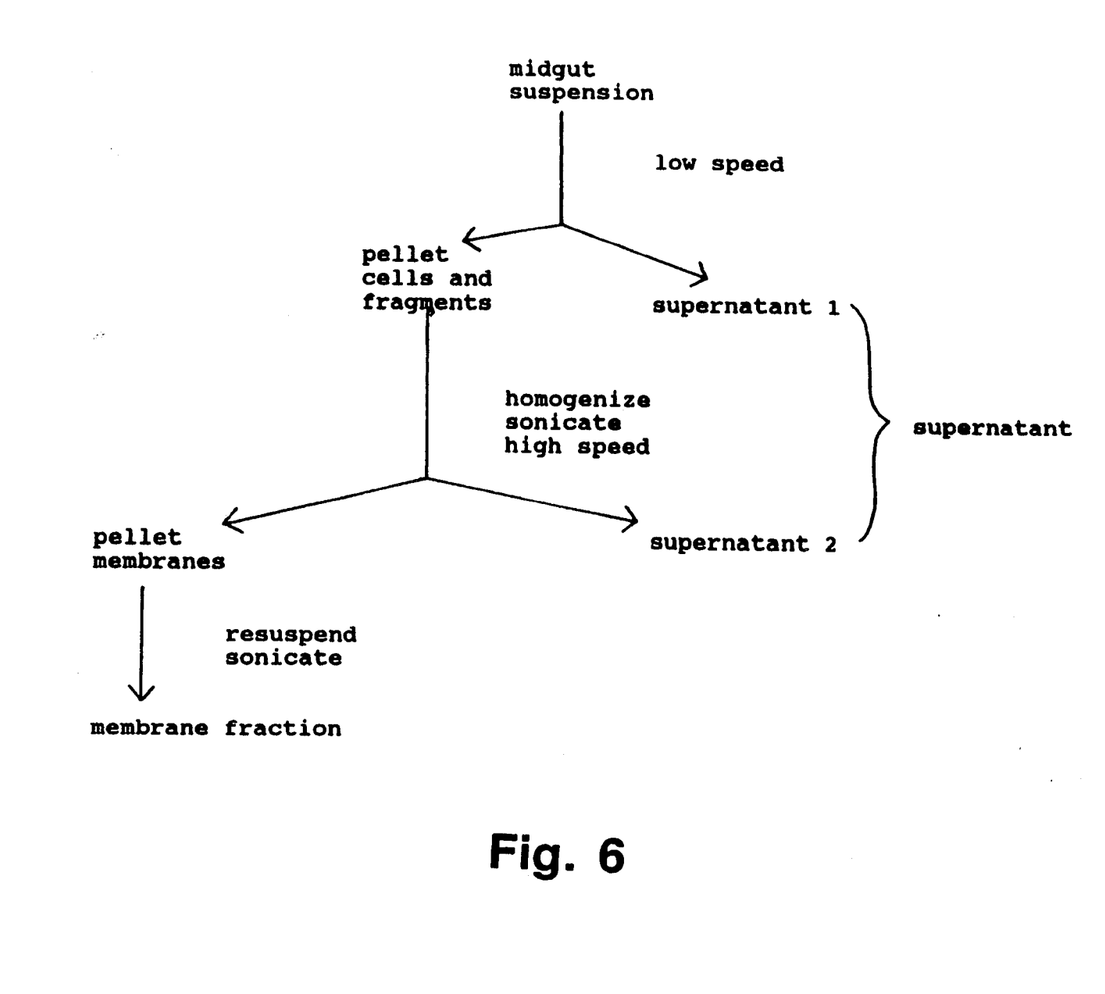
FIG. 6 shows a diagrammatic representation of the preparation of flea midgut supernatant.

Frozen midguts were thawed on ice in 1.5 ml microfuge tubes, which were then spun at a low speed to pellet the midguts. The supernatants were removed and pooled. The midguts were resuspended in buffer and pooled into groups of 1,000 in a glass/glass tissue homogenizer and homogenized on ice to a smooth suspension, followed by sonication for two minutes. The sonicated material was pooled and spun at $100,000 \times g$. The supernatant was removed and pooled with the original low-speed supernatant, and the pellet, containing the membrane fraction, was resuspended in buffer by homogenizing and sonicating. A schematic representation of this procedure is shown in FIG. 6.

Aprotinin was added to the samples at a concentration of 20 μg/ml and the remaining materials, after removal of samples for protein determinations and protease assays, were stored at $-70°$ C. until formulation. In each 1,000 midgut aliquot, the protein content of unfed membrane was ∼333 μg, fed membrane ∼2 mg, and fed supernatant ∼900 μg.

EXAMPLE 2

Formulation of Vaccines

RIBI adjuvant consisting of cell wall skeleton (CWS) monophosphoryl lipid A (MPL), and trehalose dicorynemycolate (TDCM) was obtained from the manufacturer and stored at 4° C. Prior to use, the vial was warmed to 37–40° C. in a water bath and vortexed vigorously to remix. To formulate 1.0 ml final dose of vaccine for dogs, 40 μl of the adjuvant/oil concentrate was removed and placed in the bottom of a Potter-Elvehjem grinding tube. The antigen preps were thawed, briefly sonicated and Bradford protein assay was performed prior to formulation. The desired concentration (100 μg) of antigen was added in a volume which is approximately 10% of the final volume (i.e., 1 ml). A Teflon pestle was placed in the grinding tube and, using a ⅜" drill, the oil/antigen mixture was ground thoroughly (2–3 min. at 1000–1500 rpm) forming an oil paste. Leaving the pestle in place, 0.9 ml of 0.1% v/v Tween 80 in saline were added to the tube. With the drill running, up-and-down strokes of the grinding tube to homogenize the oil/Tween 80 saline were used. The homogenization process was continued for 6–8 minutes to form a good emulsion. A 1.0 ml final volume of vaccine prepared in this manner contains 100 μg antigen, 150 μg cell wall skeleton (CWS), 100 μg monosphosphoryl lipid A (MPL), and 75 μg of trehalose dicorynemycolate (TDCM) in a 4% squalene (oil)-in-water emulsion.

EXAMPLE 3

Immunizations

Vaccine preparations were mixed by Vortexing prior to injection. Animals were injected intramuscularly with a total of 0.5–1 ml of each vaccine in 2 sites, 0.25–0.5 ml in each hind leg. A detailed protocol for a canine immunization study is as follows:

Day 0—Prebleed and 1° Immunization
Day 21—Bleed and 2° Immunization
Day 28—Bleed
Day 47—3° Immunization
Day 54—Bleed
Day 64—4° Immunization
Day 71—Bleed
Day 73—5° Immunization
Day 80—Bleed
Day 100—6° Immunization
Day 103—Bleed and Challenge
Day 110—Comb off.

The animals were bled from the jugular vein. 5–10 ml of blood were collected per bleed, allowed to clot at room temperature, and refrigerated overnight. Serum was collected and assayed using an ELISA.

The antigen used in the ELISA was either unfed flea midgut membrane, fed flea midgut membrane, or fed flea midgut supernatant prepared as described above. Antigen was diluted to 2 mg/ml in phosphate buffered saline (PBS) followed by addition of Triton X-100 to a final concentration of 0.1%. The antigen was further diluted to 5 μg/ml in carbonate buffer (0.05M carbonate/bicarbonate, pH 9.6). 50 μl of the final solution were added to each well of a 96-well plate and incubated overnight at 4° C. The antigen solution was removed and plates were washed×3 with PBS+0.05% Tween 20 (PBS/Tween). Each well received 100 μl PBS+1% BSA (PBS/BSA) and plates were incubated at room temperature (RT) for 1 hour. The solution was removed and 50 μl PBS/BSA were added to all wells but the first row. The first well in each column received 67.5 μl PBS/BSA+7.5 μl serum (yielding a 1/10 starting dilution). 25 μl was transferred serially from the first well in each row and the canine antisera were incubated at RT for 2 hours. The wells were washed×3 with PBS/Tween. 50 μl of diluted conjugate were added to each well (goat anti-dog Ig-peroxidase conjugate, Cappel, 1:1000 in PBS) and incubated for 1 hour at RT. Wells were washed×3 with PBS/Tween. 50 μl substrate was added per well (substrate is 1 tablet [10 mg] ABTS in 20 ml 0.18M citrate/phosphate, pH 4.0,+6 μl 30% $H_2O_2$) and incubated for 30 minutes at RT in the dark. 50 μl Stop Buffer (0.18M citrate/phosphate, pH 2.0) were added per well and the O.D. was read at 405 nm.

The challenge was initiated when the canine antibody titers against flea antigen were determined to be maximal as assayed by ELISA.

EXAMPLE 4

Results of Challenge

Each dog was fitted with a plastic Elizabethan collar and housed individually in a stainless steel cage with a slatted floor and with a waste collecting pan place below the floor. 100 newly emerged adult cat fleas were infested on each dog on day 0 of the challenge period. The fleas are administered at a ratio of 4 females:1 male. Flea populations on each dog were assessed by area counts on days 1, 3, and 7. "Area counts" involve counting fleas in 5 areas on the dogs (right side behind shoulder, left side behind shoulder, dorsal midline, tail-head, and inguinal area). On day 7, after the last area count, fleas were combed off the dogs and enumerated. The fecundity of surviving fleas was assessed by placing the survivors in separate glass jars (one jar per dog) overnight. The number of eggs produced was visually enumerated the following day. To assure that all fleas were obtained in the comb-off, dogs were sprayed with an alcohol-based pyrethrin flea spray and dead fleas removed by vigorous combing and brushing.

EXAMPLE 5

Alternate Immunization Protocol

Because of moderate to severe local reactions obtained in several vaccinates after the second immunization, the quantity and complexity of adjuvant in subsequent immunizations was altered. As it became clear that the local reactions could be controlled by an alteration in the immunization procedure (i.e., changing needles after drawing up vaccine and after first injection for each dog and holding the needle in the injection site for several seconds prior to removal), the concentration of adjuvant was gradually increased back to the original dosage. The exact adjuvant composition for each immunization in one study was as follows:

| Immunization | Composition of Adjuvant |
|---|---|
| 1° | 150 μg cell wall skeleton (CWS)<br>100 μg monophophoryl Lipid A (MPL)<br>75 μg trehalose dicorynemycolate (TDCM)<br>in 4% Squalene in water (1 ml dose in 2 sites) |
| 2° | As above |
| 3° | 2% Squalene in water (1 ml dose in 2 sites) |
| 4° | 50 μg MPL<br>in 2% Squalene in water (1 ml dose in 2 sites) |
| 5° | 18.75 μg CWS<br>12.75 μg MPL<br>9.4 μg TDM<br>in 0.5% Squalene in water (0.5 ml dose in 2 sites) |
| 6° | As in first immunization (0.5 dose in 2 sites) |

With proper administration the adjuvant composition of the 1st, 2nd, and 6th doses is preferred.

EXAMPLE 6

Preparation of Antibodies in Rabbits

Rabbits were immunized with membrane or supernatant antigen preparations from fed and unfed fleas. The first immunization was of 100 μg of antigen in complete Freund's adjuvant, delivered intramuscularly to two sites. Secondary and booster injections were composed of 100 μg of antigen in incomplete Freund's adjuvant. Rabbits were bled at 7 and 14 days after immunizations; titers by ELISA against homologous antigens reached around 1/100,000 following the second immunization and did not rise further following subsequent immunizations.

Antisera were precipitated with ammonium sulfate using standard techniques and, following dialysis, were made up to the original volume with PBS. Antisera from the second immunization onward were used to assess killing in the artificial system.

EXAMPLE 7

Effect of Antibodies on Flea Feeding

Feeding of fleas artificially followed many parameters suggested by the standard Wade and Georgi report, but incorporated some modifications. Rutledge type feeders were used (purchased from Lillie Glassblowers, Smyrna, Georgia). These consist of an outer jacket through which water heated to 37°–38° C. is circulated. Citrated bovine blood (T. Morris) was contained in the inner chamber, the bottom of which is normally open, but which is closed off by the flea chamber. The flea chamber was designed to contain the fleas and to allow access to the blood through a parafilm membrane, whereas the Wade and Georgi system was designed to collect eggs and produce fleas artificially. The flea chamber consisted of a normal tissue culture dish (52 mm) with lid. A hole of 40 mm diameter was cut into the lid, and in later cases a hole of 25 mm diameter was cut in the base and was sealed off with nylon gauze of a 400 μm gauge. Dog or cat fur was placed in the chamber, along with 25–50 fleas prefed on cats. The lid was placed on the chamber and the top covered in Parafilm. The parafilm-sealed chamber containing the fleas was then abutted onto the base of the feeder and held in place by clamps. 10 ml of citrated bovine blood was added to the feeder, along with 0.5 ml of ammonium sulfate precipitated immunoglobulin (diluted to the original volume of serum) and 250 μl of guinea pig complement (Pel freez). 24 h later another 100 μl of complement was added and at 48 h the system was dismantled and cleaned, and flea mortality or survival was assessed. The live fleas were then returned to the chambers, and the procedure repeated up to day four or beyond. Chambers including the gauze bottom were placed in a humidified room which was maintained at 50–75% humidity using a household humidifier. Chambers without the gauze bottom were completely sealed in parafilm. In both situations, greater than 95% of fleas can be seen to have fed after a 24 h period.

Figure 1:
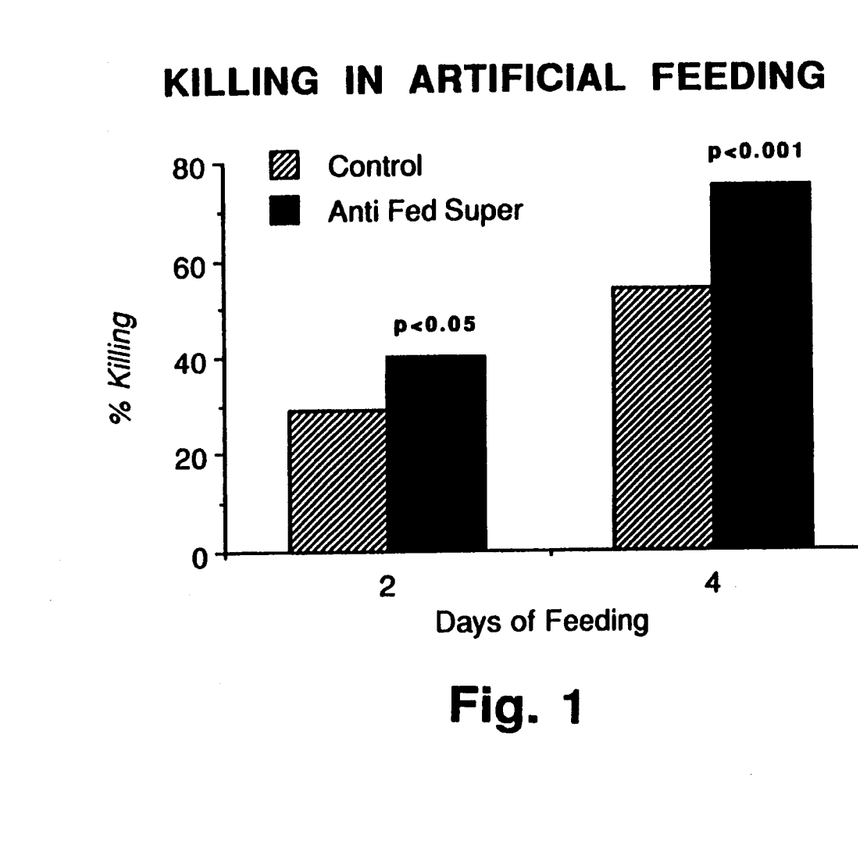
FIG. 1 shows the ability of antibodies raised to fed midgut supernatants to effect killing of fleas in an artificial feeding protocol.
Figure 2:
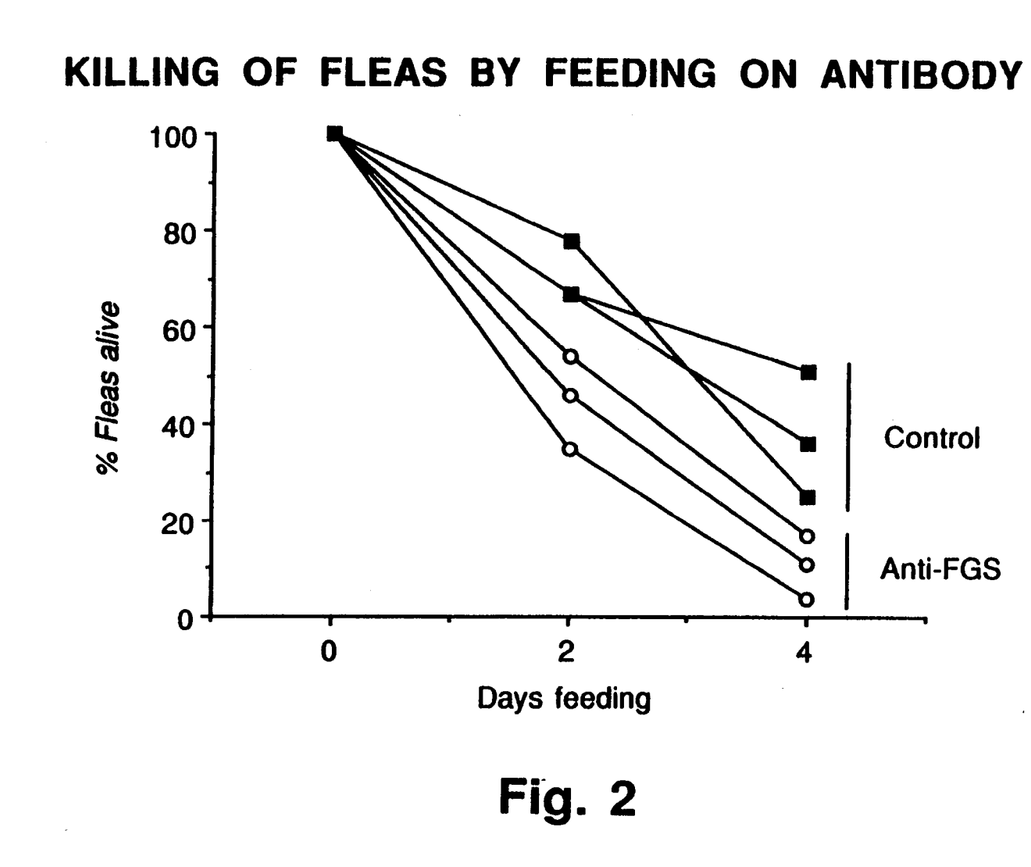
FIG. 2 shows the time course of flea killing in an artificial feeding study which includes antibody to flea midgut supernatant (FGS=fed-gut supernatant).

Test immunoglobulin preparations were always compared with control preparations prepared from rabbits given adjuvant alone. Significant killing was seen using immunoglobulin prepared from fed supernatant immunized rabbits. Mean results from seven experiments (seven test chambers, seven control chambers) showed that on day 2, 29% of fleas in control chambers, and 40% of fleas in test chambers were dead ($p<0.05$, Yates' corrected Chi squared test) and by day 4, 54% of controls, and 75% of test fleas were dead ($p<0.001$). These results are shown in FIG. 1. FIG. 2 shows the time dependence of results obtained in a triplicate experiment in which three control chambers (Ig from rabbits receiving adjuvant only) and three test chambers (Ig from rabbits receiving adjuvant plus fed-gut supernatant antigen) were used simultaneously.

EXAMPLE 8

Vaccine Effectiveness

Figure 3:
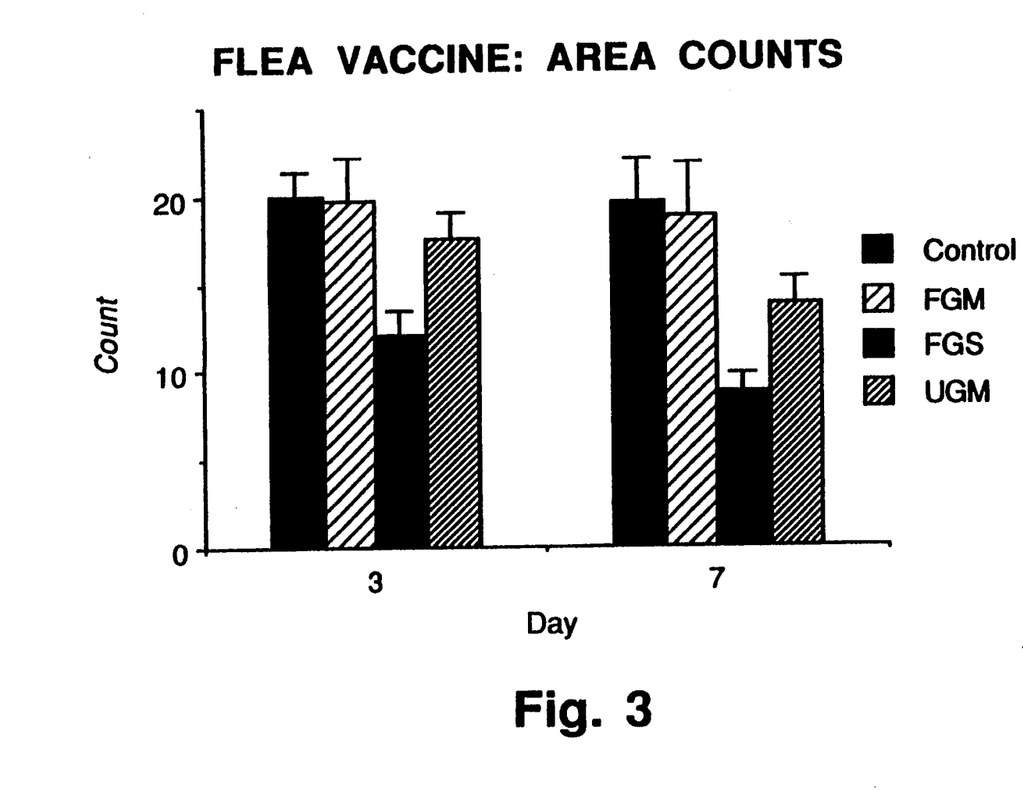
FIG. 3 shows the effect of flea midgut supernatant vaccine on the area count of fleas on vaccinated hosts (FGM=fed-gut membrane; FGS=fed-gut supernatant; UGM=unfed-gut membrane).

Area counts were shown in a previous study to correspond to some extent with the total number of fleas on the dog, although as total flea number decreased, area counts tended to decrease to a lesser extent, presumably because the few remaining fleas tend to prefer those areas and migrate into them. Area counts in the dog immunization study were performed on day 3, and on day 7, the day of the final comb off. The results are shown in FIG. 3 and it can be seen that area counts in the fed supernatant group are significantly reduced by day 3, from a mean of 20, to a mean of 12 ($p<0.01$, Student's T test), and remain reduced at day 7 from a mean of 19.6, to a mean of 8.8 ($p<0.01$, Student's T test). This reduction in the area counts to less than half of control values is unexpectedly greater than the real killing effect as ascertained by counting the total fleas on the animal, and could be interpreted as indicating some damage to surviving fleas, decreasing their movement around the animal. The possibility of damage to at least some of the fleas remaining on the animal is borne out in the fecundity results below.

Figure 4:
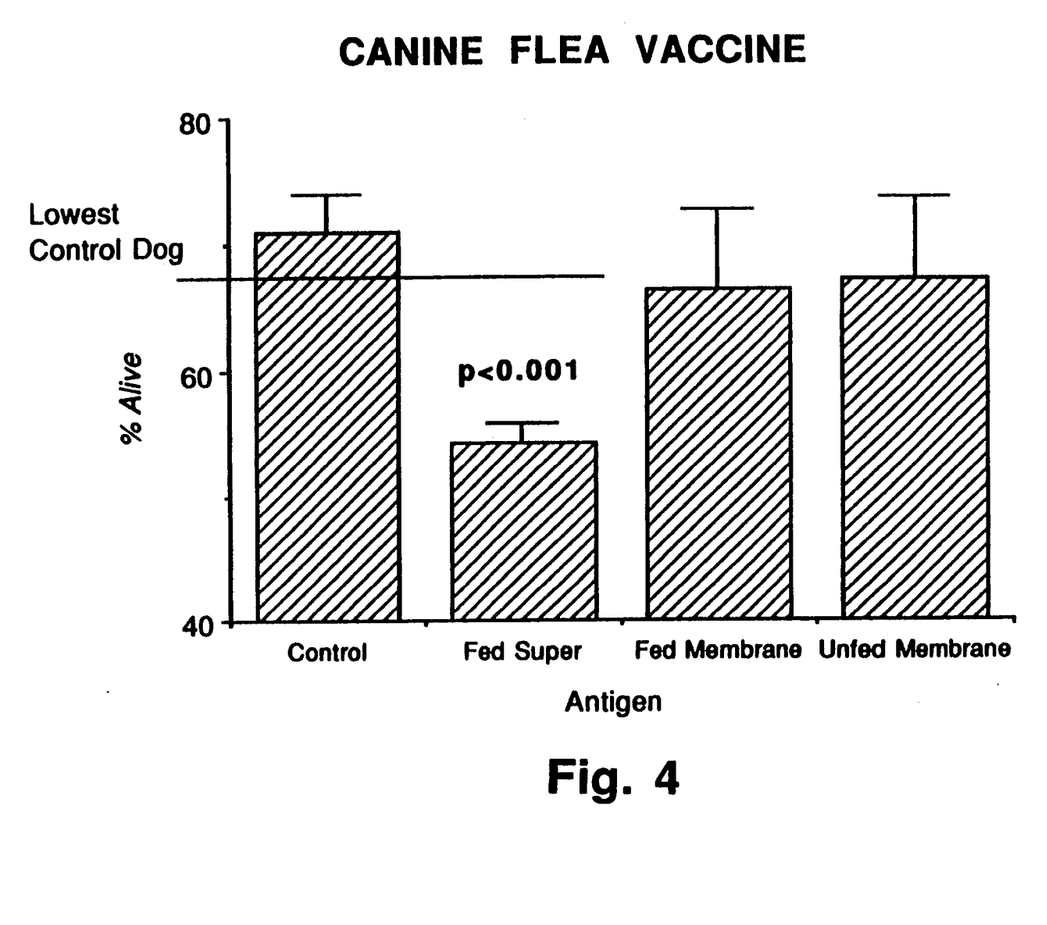
FIG. 4 shows the effect of flea midgut supernatant vaccine on final comb-off counts of fleas on vaccinated hosts (fedmembrane=fed-gut membrane; fedsuper=fed-gut supernatant; unfed membrane=unfedgut membrane).

The total number of fleas remaining on the animals after 7 days was ascertained following a thorough combing of the dogs, followed by an alcohol-based insecticide spray, further combing, and an examination of pans under the dogs on the following day. A mean of 71 fleas was retrieved from the control dogs, with the range being from 67 to 75 and the standard deviation 3.08. A mean of 54.8 fleas were retrieved from the fed supernatant immunized animals, with the range being 46 to 63, and the standard deviation 6.76. This reduction is significant ($p<0.002$, Student's T test) (FIG. 4). The mean number of surviving males in the fed supernatant group was 13.6 (45.3%) and of females was 41.2 (58.9%). In the control group these figures were: males, 16.8 (56%); females, 54.2 (77.4%). Males were thus reduced by 19% and females by 24% by feeding on fed supernatant immunized dogs. This difference might reflect the fact that females are known to take in larger amounts of blood (Dryden, personal communication).

Figure 5:
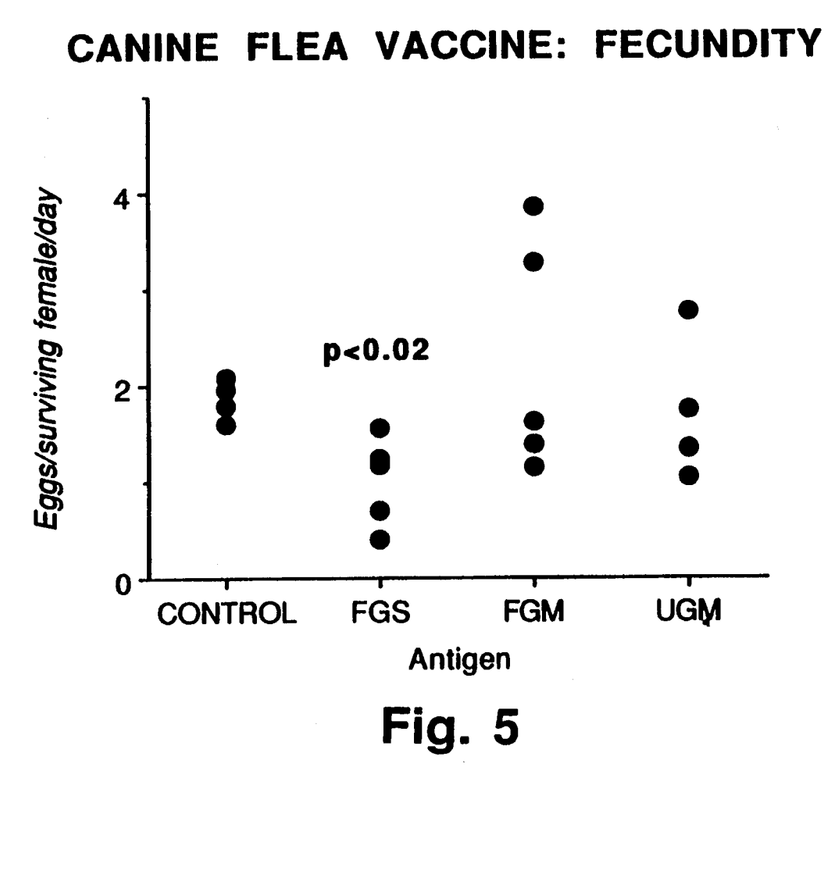
FIG. 5 shows the fecundity of fleas recovered from animals with flea infestations which have or have not been vaccinated with flea antigen preparations (FGM=fed-gut membrane; FGS=fed-gut supernatant; UGM=unfedgut membrane).

Fleas combed off each of the dogs after 7 days were kept in separate tubes overnight and the number of eggs produced were counted the following day. The figures for the number of eggs per female flea are shown in FIG. 5. Fleas from the fed supernatant group produced a mean of 1.016 eggs per female flea, whereas control fleas produced a mean of 1.85 eggs per female flea. This 45% reduction in fecundity is statistically significant ($p<0.02$, Student's T test).

We claim:

1. A composition for protection of a mammalian subject against infestation by fleas, which composition consists essentially of an amount of the soluble components of fed or unfed flea midgut effective to reduce said infestation wherein said composition is prepared by a method which comprises     homogenizing and then sonicating fed or unfed flea midgut to obtain a homogenate/sonicate;

separating said homogenate/sonicate into a supernatant fraction consisting essentially of the soluble components of said homogenate/sonicate and a fraction containing membranes and fragments thereof by centrifuging said homogenate/sonicate at at least about 100,000×g to obtain said supernatant and a pellet; and     recovering the supernatant containing said soluble components.

2. The composition of claim 1 wherein said supernatant is derived from fed flea midgut.

3. A method to reduce the flea population in the environment of a mammalian subject, which method comprises administering to said subject an effective amount of the composition of claim 1.

4. A method to prepare a composition effective in protecting mammalian subjects against flea infestation which method comprises homogenizing and then sonicating fed or unfed flea midgut to obtain a homogenate/sonicate;

separating said homogenate/sonicate into a supernatant fraction consisting essentially of the soluble components of said homogenate/sonicate and a fraction containing membranes and fragments thereof by centrifuging said homogenate/sonicate at at least about 100,000×g to obtain said supernatant and a pellet; and     recovering the supernatant containing said soluble components.

* * * * *